United States Patent
Krause et al.

(10) Patent No.: US 7,863,471 B2
(45) Date of Patent: Jan. 4, 2011

(54) PROCESS FOR THE TRANSESTERIFICATION OF ESTERS

(75) Inventors: Eberhard Krause, Hohen Neuendorf (DE); Valentin Rohm, Munich (DE)

(73) Assignee: Krause-Rohm-Systeme AG, Munich (DE)

( * ) Notice: Subject to any disclaimer, the term of this patent is extended or adjusted under 35 U.S.C. 154(b) by 282 days.

(21) Appl. No.: 12/298,487

(22) PCT Filed: Apr. 25, 2007

(86) PCT No.: PCT/EP2007/054062

§ 371 (c)(1),
(2), (4) Date: Oct. 24, 2008

(87) PCT Pub. No.: WO2007/125069

PCT Pub. Date: Nov. 8, 2007

(65) Prior Publication Data

US 2009/0259067 A1 Oct. 15, 2009

(30) Foreign Application Priority Data

Apr. 28, 2006 (DE) .................. 10 2006 019 883

(51) Int. Cl.
*C07C 67/00* (2006.01)
*C01F 7/04* (2006.01)
(52) U.S. Cl. .................. 554/124; 554/74; 423/119; 423/121

(58) Field of Classification Search .................. None
See application file for complete search history.

(56) References Cited

U.S. PATENT DOCUMENTS 4,017,425 A * 4/1977 Shiao .................. 252/184

FOREIGN PATENT DOCUMENTS

| DE | 329972 | 11/1920 |
|---|---|---|
| DE | 4114883 A1 | 11/1992 |
| EP | 0093339 A2 | 11/1983 |
| GB | 634411 | 3/1950 |
| WO | 2005026080 A1 | 3/2005 |
| WO | 2005063954 A1 | 7/2005 |

OTHER PUBLICATIONS

Kurdowski et al., Chapter 6—Red Mud and Phosphogypsum and thier field of application, 1997, Waste Materials used in concrete Manufacturing, Noyes Publications, pp. 32.*

* cited by examiner

*Primary Examiner*—Jafar Parsa
*Assistant Examiner*—Yate' K Cutliff
(74) *Attorney, Agent, or Firm*—Barlow, Josephs & Holmes, Ltd.

(57) ABSTRACT

The invention relates to a method for transesterification of at least one component comprising at least one ester group with at least one component comprising at least one hydroxyl group, wherein the red mud produced in the Bayer process used for producing aluminum is added to the method as a reaction-promoting component. The invention also relates to the use of carboxylic acid salts produced during the transesterification method as plant treating agents and as detergents in cleaning and washing agents. The invention also relates to the use of dealkalized red mud obtained by means of the method according to the invention as the iron-contributing component of an iron fertilizer which can be used in particular in agriculture and to which limestone can also be added.

35 Claims, No Drawings

PROCESS FOR THE TRANSESTERIFICATION OF ESTERS

TECHNICAL FIELD

The invention relates to a method for transesterification of at least one component including at least one ester group with at least one component including at least one hydroxyl group.

PRIOR ART

In the aluminum production according to the Bayer process, $Al_2O_3$ is released from finely grinded bauxite with the aid of caustic soda lye. After seeding with crystallization nuclei, pure $Al(OH)_3$ (gibbsite) is precipitated from the sodium aluminate solution obtained therein, from which electrolytic metallic aluminum is obtained after further process steps. There remains a mixture, which chemically considered is mainly composed of ferric oxides or hydroxides, respectively, titanium oxides, alumina residues, quartz sand, calcium oxide, sodium oxide and residual caustic soda lye. Due to its red color caused by ferric oxide, this residue is designated as "red mud".

According to the quality of the used bauxite, 1 to 1.5 tons of red mud arise as non-avoidable attendant to each produced ton of aluminum. The amount arising therein each year is several millions of tons and presents a serious environmental and disposal problem together with the already present red mud waste. The main problem is the high alkalinity of the red mud due to its content of caustic soda lye with pH values between 11 and 13. Moreover, toxically acting aluminum ions together with iron compounds present a great danger to the ground water and additionally aggravate environmentally compatible storage. Currently, the disposal of the red mud is effected substantially by storing in sealed disposal sites. The caustic soda lye exiting on the floor of the disposal site is collected and recycled into the Bayer process. However, this form of storage is costly and expensive, since large disposal site areas and plants are required and high cost arise for the transport of the red mud. Additionally, the long-term cost arising by the deposition can only be difficultly calculated and present an additional economical problem.

Numerous attempts have been made to convert the red mud considered as waste product heretofore into utilizable reusable materials and to feed to economical utilization. Therein, in the first place, each useful approach has to aim at reduction of the highly alkaline pH value, but should also exploit the potential contained in the red mud as much as possible and offer a comprehensive utilization of the obtained components in the second place. The processing is aggravated in that the particles of the red mud have a very small diameter on average in the range between 0.1 μm and 1 μm caused by the production process.

A newer method by Virotec International LTD, protected as "Basecon™ technology", achieves a reduction of the pH value to about 9 by the conversion of red mud with sea water, and thereby opens various possibilities of application for the dealkalized red mud such as the employment as flocculating agent or as treating agent for acidic wastewaters or acidic soils, respectively.

The circumstance that the use of about 1 million of tons annually within the scope of this method corresponds to less than 2% of the annual production and thus it is not suitable to cope with the annually arising amount of red mud, and especially does not present any solution for the already deposited red mud waste, is to be considered disadvantageous in this method. Furthermore, it is to be considered disadvantageous that wide use of the various reusable materials contained in the red mud does not occur, and thus the present economical and ecological potential is not exploited.

Therefore, the object of the present invention is to provide a method, which allows material utilization of the already deposited as well as of the annually newly arising red mud as wide as possible.

PRESENTATION OF THE INVENTION

The object is solved according to the invention by a method for transesterification of an ester with an alcohol using red mud as reaction-promoting component, including the features of claim 1.

Advantageous developments with convenient and non-trivial further developments of the invention are described in the further claims.

According to the invention, red mud is employed as a reaction-promoting component in a method for transesterification of one or more compounds including at least one ester group with one or more compounds including at least one hydroxyl group. Such a method offers very different advantages. Besides large amounts of caustic soda lye, red mud also contains various metal oxides and hydroxides and thus serves as a highly basic and catalytically active reaction component transferring the alcoholic compounds into alcoholates and permits the transesterification reaction. Besides this basic ester alcoholysis, at the same time, basic ester hydrolyses also proceed to the residual water bound in the red mud, in which the components containing ester groups are cleaved into the corresponding carboxylic acids and alcohols. In this reaction, hydroxide ions are consumed such that the pH value of the red mud decreases. Consumption of alkaline components in the course of the reaction would present a clear disadvantage under normal conditions, since either the alkaline components have to be replaced constantly or the reuse of the catalyst would have to be abandoned. However, in the method according to the invention, these facts are utilized in advantageous manner, since red mud is available in virtually unlimited amount and the alkaline components contained in the red mud constitute no cost factor, but on the contrary the essence of the problem and are to be consumed in an amount as large as possible. The method according to the invention therefore provides in one step transesterified products, free alcoholic compounds, salts of free carboxylic acids and dealkalized red mud, which usually can be separated from each other very simply. In this manner, the method according to the invention permits a comprehensive material utilization of red mud obtaining various reusable materials, wherein both already deposited and newly arising red mud can be employed without problem and be utilized in great amounts.

In an advantageous development of the invention, the method includes the following steps: a) mixing the component including the at least one ester group, the component including at least one hydroxyl group and the red mud, b) heating and/or mixing the produced mixture for the duration of a predetermined time interval, and c) separating at least one first liquid phase from at least one second phase, wherein the liquid phase includes at least one carboxylic acid alkyl ester and the second phase includes at least dealkalized red mud. In many cases, transesterifications are already started by mixing the reactants. However, often, these reactions proceed slowly such that heating the reaction mixture becomes required. Therefore, the component including an ester group, the alcoholic component and the red mud are mixed and subsequently heated with stirring for a certain time. In this manner, the required activation energy can be supplied to the reaction and a conversion of the educts as fast and complete as possible can be achieved with large neutralization of the red mud. After completion of the reaction, the individual reaction products separate into at least two different phases and can be separated from each other. Therein, a first liquid phase contains at least one carboxylic acid ester as a product of the transesterification. The dealkalized red mud settles in most cases without problem within short time and forms a solid phase, in which also salts of the free carboxylic acids can be present. According to educt and product composition and reaction sequence, the red mud can also be present as a polymorphous, colloidal suspension due to its small particle size instead of solid precipitate, but which has a clear phase boundary line to the first liquid phase and is simply identifiable by its intense red coloration.

In another advantageous development of the method according to the invention, the component including at least one ester group is a vegetable oil. Vegetable oils predominantly consist of mono-, di- and triglycerides and are available worldwide in great variety and in large amounts. Besides various other conceivable vegetable oils, especially palm oils, soya oils or rape oils are suitable as an educt for the method according to the invention, since economically considered they present inexpensive and globally available educts, and are to be appreciated as largely unproblematic under environmental aspects due to their biological degradability.

The German Federal Environmental agency for example categorizes vegetable oils in the water hazard classification 1 and thus as only slightly hazardous to water. Since, within the scope of the method according to the invention, it is not required to employ highly pure oils, by use of roughly pressed or contaminated vegetable oils, additional cost can be saved. In this manner, even waste products of the vegetable oil industry can be provided to advantageous utilization and also be used for obtaining reusable material. Moreover, vegetable oils have a certain portion of free fatty acids, by which already a part of the alkaline red mud components can be neutralized. Therein, the corresponding salts of the fatty acids develop, which ultimately are soaps. According to the invention, they can be separated as an additional reusable material and be used for various purposes. A reusable material also developing during this method is glycerin, which is released by the basic ester hydrolysis from the glycerides contained in the vegetable oil. For example, glycerin finds a use in the pharmaceutical and cosmetic industry as a valuable basic or raw material and can be obtained in large amount by the method according to the invention. All main and by-products of the reaction can thus be further used as an educt of the method according to the invention in employment of vegetable oils and present themselves a reusable material.

In another advantageous development of the method according to the invention, the component of the transesterification including at least one hydroxyl group includes one or more alcohols of the group of methanol, ethanol, propanol and butanol. Combined with the use of vegetable oil as the component including ester groups, fatty acid alkyl esters can be obtained in particularly simple manner, which present the currently most environmentally compatible fuel for diesel vehicles as the so called biodiesel. The advantages of the product biodiesel are known to the person skilled in the art. Biodiesel has appreciably lower exhaust gas values than fossil fuel, is almost sulfur-free, nontoxic, $CO_2$-neutral and biologically degradable. Additionally, the exhaust of carbon black of an automobile filled up with biodiesel is halved.

A simple and cost-effective reaction sequence is achieved in the method according to the invention in that either the component including ester group or the component including hydroxyl group functions itself as a solvent and is used for dissolving or suspending the remaining components, respectively.

In another advantageous development of the method according to the invention, in the first method step a), first the red mud is suspended in the component including the hydroxyl group, and subsequently the component including the ester group is mixed thereto. Thereby, sticking of the red mud can be prevented and a mixture as homogenous as possible can be produced, which is the premise for a fast conversion of the reactants.

In another advantageous development of the method according to the invention, the temperature of at least one component is adjusted to a predetermined temperature value before admixture thereof. Thereby, it has been manifested advantageous to preheat especially the component including the ester group before admixture thereof. For example, this can be effected by use of a pipe heat exchanger and presents a simple method to activate the reaction on the one hand and to return thermal energy arising during the method into the process in energy and cost saving manner on the other hand.

In another advantageous development of the method according to the invention, the reaction mixture is heated to about 60° C. for the period of one hour preferably with stirring in step b). In most cases, thus, optimum compromise between economy, reaction duration and maximization of yield is achieved.

In another advantageous development of the method according to the invention, after step a) and particularly during step b), a fourth component is collected, which includes at least one component gaseous at room temperature and normal pressure. Gaseous compounds collected in step b) can be further utilized advantageously in manifold manner. Therein, one possible use is in the thermal utilization of reaction gases and the recycling of the thermal energy obtained therein into the process, for example for preheating the educts or for heating the reaction mixture.

In another advantageous development of the method according to the invention, after step b), a fifth and a sixth component are separated from the mixture in an additional step d), wherein the fifth component includes at least one compound of the group of the $C_1$ to $C_4$ monoalcohols and the sixth component includes at least water. Depending on the employed educts and the selected process sequence, it has proven advantageous to remove the developed or non-reacted alcohols, respectively, or those employed as a solvent from the reaction mixture after execution of the reaction. Therein, preferably, present residual water is also removed. In this manner, recovery of reusable materials can be achieved on the one hand, and the subsequent separation of the at least two phases to be performed in step c) can be facilitated and accelerated on the other hand.

In another advantageous development of the method according to the invention, the additional step d) therein includes a variation of temperature and/or pressure conditions. Therein, heating the reaction mixture above the boiling point of the compounds to be removed with subsequent distillation of the fifth and sixth components presents a simple possibility. For example, if only the alcohols methanol or ethanol are to be removed together with residual water, increase of the temperature of the reaction mixture to about 98° C. on normal pressure conditions is sufficient.

In another advantageous development of the method according to the invention, the variation of the temperature conditions includes regulation of the temperature value to about 80° C., and the variation of the pressure conditions includes regulation of the pressure value to a value greatly reduced with respect to the normal pressure, especially below 250 hPa. These variations of the temperature and pressure conditions result in appreciable acceleration of the distillation process. These variations are advantageous especially if the fifth component also includes longer-chain alcohols such as propanol or butanol, since they have boiling points of 97° C. and 118° C., respectively. However, the variations are not restricted to the application to these compounds and are also conceivable for removing water, methanol or ethanol. The variation of the pressure conditions can preferably be achieved with the aid of customary diaphragm pumps. Suitable parameter values for example for distilling an ethanol-water mixture are a temperature of about 80° C. and a pressure below 250 hPa.

In another advantageous development of the method according to the invention, the method includes an additional step e) after step d), in which the fifth and sixth component collectively separated in step d) is separated. For example, if in step d) an ethanol-water mixture is collectively separated, it has manifested advantageous to separate again the distilled ethanol-water mixture in the sense of a long-term raw material utilization into its individual components and to use the alcohol for example for another method run. However, application of step e) to all of the separable mixtures such as for example methanol-water or propanol-water is also conceivable.

In another advantageous development of the method according to the invention, step e) includes at least one process for separating homogeneous mixtures, especially an extractive distillation process. Since alcohol and water often form homogeneous, azeotropic mixtures, which cannot be completely separated by simple rectification, for this case, the use of a suitable separating process is provided. Therein, besides extractive distillation processes, all of the other suitable separating processes such as for example membrane separating processes also lend themselves. In the extractive distillation process, a third compound is admixed to the azeotropic boiling binary mixture as an entrainer, thereby producing a ternary mixture. Ideally, glycerin lends itself as an entrainer, which presents a product of the reaction in the use of vegetable oils as a transesterification educt, for example, and therefore is available in great amount. However, further suitable compounds such as paraffin oil or ethane diol are also conceivable as entrainers.

Another advantageous development of the invention results if step c) includes at least one distillation and/or filtering and/or sedimentation and/or decantation process. The separation of the first liquid phase from the second phase containing the red mud by a decantation step advantageously exploits the different values of specific gravity of the individual reaction products. Thus, the individual components of the reaction mixture can be practically quantitatively separated from each other in simple and inexpensive manner. For separating the mixture, sedimentation and filtering processes are also suitable. Separation with the aid of distillation processes is also conceivable in order to advantageously separate volatile from non-volatile components, especially the red mud.

In another advantageous development of the method according to the invention, at least one sedimentation process includes separation of red mud sediments.

Another advantageous development of the method according to the invention includes at least one filtering process, wherein the filtering step is effected by means of red mud sediments. By execution of sedimentation and filtration in series, the red mud sediments obtained in the first sedimentation step can advantageously constitute the active filter component in the following filtering step. Due to the small particle size of the red mud, thus, one obtains an extremely powerful filter element with high retention action for solid components in particularly simple and cost-reducing manner. Instead of a sedimentation step, it is also conceivable to first filter out red mud with a coarse filter element and to use it as a filter element in further filtering steps.

In another advantageous development of the method according to the invention, at least one filtering process includes a filtering step by means of a vacuum filter. Since, in such case, it is not required to perform an additional sedimentation step before filtration, thus, appreciable saving of time and cost reduction associated therewith due to the higher throughput of reaction mixture result.

In another advantageous development of the method according to the invention, the vacuum filter is formed in multiple stages. Due to the small particle size of the red mud, it has manifested advantageous to use a multi-stage vacuum filter for avoiding occlusion of a single filter element.

In another advantageous development of the method according to the invention, at least one part of the filter cake produced by the filtering step is thermally utilized and especially combusted. The main component of the filter cake consists of red mud, which binds various combustible reaction products due to its large surface area. If one uses for example vegetable oil as component of the method including ester group, thus, the red mud filter cake contains glycerin, soaps and carboxylic acid esters as combustible components besides residues of the alcoholic component after completion of the reaction.

In another advantageous development of the method according to the invention, plastic and/or wood and/or biological waste is admixed to the filter cake before thermal utilization. Besides admixture of combustible waste products such as plastic, wood or biological waste, the admixture of straw, pulp or combustible organic waste is also conceivable. This step thus also opens the possibility to make available material categorized as waste to an advantageous further use.

In another advantageous development of the method according to the invention, the thermal energy arising in the thermal utilization is returned to at least one of the method steps a) to c) and/or optionally d) and/or e). The thermal energy can for example serve for preheating an educt of the reaction before admixture thereof, for heating the reaction mixture to the predetermined temperature value or for performing a separating step following the reaction, especially a distillation step. Alternatively, utilization of the thermal energy for current generation is also conceivable.

In another advantageous development of the method according to the invention, the method includes an additional step f) after step c), which includes separation of at least one component including at least glycerin. For example, if one uses vegetable oils as component including ester group as an educt in step a) of the method, thus one obtains glycerin as a reaction product of the transesterification among other things. Since glycerin itself is an important reusable material and can be further used in manifold manner, therefore, it is advantageously separated from the remaining mixture in step f).

In another advantageous development of the method according to the invention, the method includes an additional step g) after step f), in which the at least one component including at least glycerin is separated into at least two degrees of quality. This is advantageous especially if the separated glycerin does not have the purity required for direct further use. Therefore, by step g), it is ensured that the requirements of the respective purposes of further use are correspondingly considered in the processing process.

In another advantageous development of the method according to the invention, the method includes a further step h) after step c), which includes the separation of at least one salt of at least one carboxylic acid containing sodium ions from at least one separated phase. If salts of carboxylic acids containing sodium ions arise during the transesterification by basic ester hydrolysis, it is advantageously provided to separate these compounds also presenting reusable materials in the additional method step h). If for example vegetable oil is employed as the component of the method including ester group, the thus obtained carboxylic acid salts present the salts of fatty acids and are thus to be referred to as soaps.

Another advantage of the method according to the invention is in that reusable materials can be obtained from products considered as waste heretofore, and even the by-products developing during reaction, which are normally undesired, present themselves reusable materials. These additional developing reusable materials can be employed in particularly advantageous manner for various purposes of use.

Another advantageous development of the invention includes the use of the salt of at least one carboxylic acid separated in step h) and containing at least sodium ions, as a plant treating agent, especially in case of pest infestation. The use of this carboxylic acid salt as a pesticide is advantageous not only economically, since it allows the utilization of a reaction product of the method according to the invention, but also ecologically, since the carboxylic acid salts are biologically degradable and thus largely harmless under environmental aspects.

In another advantageous development of the invention, the salt of at least one carboxylic acid containing sodium ions and used as a plant treating agent is diluted with at least one solvent, especially water. Thereby, the desired target concentration can be adjusted simply and depending on situation without restriction of the action or the biological compatibility. Thus, the carboxylic acid salt can be easily applied to the plant material to be treated as an aqueous solution with the aid of usual agricultural apparatuses.

Another advantageous development of the invention includes the use of the salt of at least one carboxylic acid containing at least sodium ions and separated in step h) as a detergent, especially in cleaning and/or washing agents. The use of the separated carboxylic acid salt as a detergent is advantageously favored by the soapy character of this class of compound and allows additional economical utilization of a product of the method according to the invention.

The dealkalized red mud arising by the method has in itself a great bandwidth of possible purposes of use.

Another advantageous development of the invention includes the use of the separated, dealkalized red mud as iron-contributing component of an iron fertilizer particularly usable in the agriculture. The sufficient supply of plants with iron is of great importance especially in the agriculture, since iron promotes the chlorophyll formation and thereby the growth especially in woods and lawn. Therein, the red mud can be used in its neutral form or be specifically adjusted to a slightly basic pH value according to the purpose of employment. This is advantageous particularly with respect to the increasing acid rain, since thus regulation to the natural pH value of the soil is achieved.

Another advantageous development of the invention provides that the iron fertilizer additionally includes at least limestone. The additional admixture of limestone advantageously accounts for the requirements of the agricultural plant cultivation and combines various plant growth promoting characteristics in one product, since regulated lime supply presents the basis of each fertilization. Additionally, the admixed lime provides for regulation of the pH value of the iron fertilizer.

Further advantages, features and details of the invention appear by way of the following descriptions of several embodiments.

EXAMPLE 1

For neutralization of alkaline red mud as complete as possible, with simultaneous extraction of as many reusable materials as possible, in a first embodiment, 400 ml rape oil as component including ester groups, 100 ml ethanol (96%) as component including hydroxyl groups and 400 g red mud as reaction-promoting component are employed for the transesterification method.

First, at room temperature, ethanol and red mud are mixed and homogenized in a reaction vessel. The homogenized mixture is mixed with rape oil and heated to 60° C. with stirring. Therein, start of the reaction often is noticeable by development of gaseous compounds. After a reaction time of about one hour, the temperature is increased to about 100° C. until boiling of the mixture in order to remove excess ethanol and water from the reaction mixture. The distilled ethanol-water mixture is collected and can be separated into its individual components by methods common to the person skilled in the art. The remaining product mixture is first roughly filtered through a glass fiber filter. The filter cake containing mainly red mud is subsequently used itself as a filter body and has an excellent separating power due to the small particle size. The filtrate is filtered two more times with the aid of the red mud filter until red coloration is no longer recognizable in the filtrate. The turbid filtrate now has a neutral pH value and is transferred to a separating funnel. Within about 30 minutes to 2 hours, separation of the mixture into three phases is effected, which are separated from each other in simple manner by decanting. Therein, the first separated phase with a specific gravity of 1.22 $g/cm^2$ contains glycerin as reusable material, the second phase consists of a suspension of various fatty acid salts, and the third phase contains rape ethyl ester with a specific gravity of 0.87 $g/cm^3$ usable as biodiesel.

EXAMPLE 2

In a premixer known per se with a volume of 1 $m^3$, 0.5 t of red mud with a water portion of about 30% (w/w, corresponding to ca. 150 l) and 500 l methanol (ca. 90%) are stirred. Instead of methanol, alternatively, ethanol, another alcohol or a mixture of different alcohols can also be used. Subsequently, the alcohol/water mixture is extracted. The water content in the red mud thereby decreases to ca. 10% (w/w), thereby appreciably improving the further processing of the red mud mass. The highly alkaline alcohol/water mixture is separated into 96% alcohol and water by vacuum liquid extraction. The highly alkaline water is subsequently employed in a gas washing device following a steam generator.

In second working process, subsequently, bioalcohol with 96% ethanol is added in an amount of 250 l corresponding to two and a half times the amount required for the transesterification and stirred for a few minutes. Subsequently, the liquid mass is pumped to a transesterification reactor with ca. 1.5 $m^3$ volume and unfiltered rape oil from the press is fed in a volume of ca. 1 $m^3$. The rape oil is previously preheated to 60-70° C., which is preferably effected with the aid of heat recovery from one of the following reaction stages.

The mixture is subsequently heated to temperatures greater than 50° C., advantageously to at least 60° C., with stirring and maintained at this temperature for ca. one hour. By control of the pH value of the solution, the completion of the process can be determined in simple manner, and optionally additional vegetable oil or additional alcohol/red mud mixture, respectively, can be fed thereafter, in order to achieve a nearly complete conversion.

Subsequently, the temperature is increased to ca. 80° C. and the mixture of remaining residual water and alcohol not consumed in the transesterification is sucked off with reduced pressure at ca. 250 hPa. For pressure reduction, for example, a diaphragm vacuum pump can be used. Subsequently, separation into water and alcohol is again effected through a following liquid extraction stage. The alcohol is recycled, the water is neutral and can be utilized as normal service water.

The remaining ester/glycerin/soap mixture is pumped off through plural sediment filters, filtered and then pumped into a decanter, wherein separation into 3 phases quickly results due to the differences of specific gravity, which can each be pumped off separately and be used as an individual product. The alkali-free, neutral red mud sediment contains comparatively much combustible residual solution and is thermally utilized, optionally with addition of wood waste or the like. The mineral residue remaining after oxidation can be utilized as iron fertilizer or be further cleaved into magnetite and a cement addition component and separately be utilized.

EXAMPLE 3

Red mud from a disposal site with a water content between 24 and 27% (w/w) is first heated to ca. 60° C. in a vacuum reactor with a coarse vacuum of about 100 mbar with residual heat of a later combustion stage, thereby extracting water by vacuum distillation and extracting a major part of the water. After ca. 30 min., only a few percent of water are still contained. The dried red mud is then sucked off into a further reactor.

In the next step, methanol is added in a proportion of methanol:red mud of about 1:2 (v/w) and the mixture is intensely mixed in order to bring the methanol to all of the mineral grain surfaces and promote the formation of sodium methanolate by reaction with the NaOH chemisorbed to the surfaces. Therein, the reaction temperature is approximately between 40 and 50° C., the reaction duration is usually between 10 and 15 min.

Subsequently, vegetable oil preheated to a temperature between 50 and 70° C. preferably with waste heat of the process, for example rape, soya or palm oil, is added into the reactor in a proportion between 1:1 and 1:2 (v/w) based on red mud. The mixture temperature is maintained at 60-65° C. and the reaction is performed for about 30 min, wherein shorter reaction times are usually not reasonable due to the extremely high surface area of the red mud. During the reaction, the mixture is intensely mixed. Therein, several processes occur:

Therein, the main reaction is in the transesterification of the vegetable oil with the formation of methyl esters of the free fatty acids or fatty acids released from the vegetable oil, respectively.

The secondary side reactions substantially include saponification reactions between free caustic soda lye and free fatty acids formed by ester cleavage or already contained in the vegetable oil with formation of soap and glycerin in presence of water, the hydrolysis of proteins, phospholipids, among other things by the highly alkaline solution at the beginning of the process, as well as the neutralization of the caustic soda lye or the sodium carbonate, respectively, with formation of sodium salts of the fatty acids.

After completion of the transesterification, a non-polar solvent—for example hexane—is pumped from a reservoir into the reactor in an amount corresponding to the vegetable oil. Subsequently, all of the non-polar or predominantly non-polar components, respectively, are extracted with intense mixing, which mainly include non-reacted vegetable oil as well as the developed methyl esters.

In the next step, the extract is pumped into a sedimenter. After 20-30 min. settling time, individual, clearly separated fractions can be extracted. In the upper portion, therein, methyl esters and vegetable oil can be found, below a mixture of methanol, soap, glycerin and water, and as the last phase finally a bottom substantially consisting of neutralized red mud. The liquid fractions are extracted, wherein hexane and non-reacted methanol, respectively, are each distilled in vacuum in following reactor units and are subsequently returned into the cycle.

The excess vegetable oil and the developed methyl esters are finally finely filtered and are available as valuable products. Therein, the yield of methyl ester is usually at least 40%. Soap, glycerin and water can be converted in a further reaction step, wherein soda, water and hydrocarbons develop, which can be collected and further used as additional reusable materials.

The bottom is also pumped off, optionally two or multiple times extracted with hexane for increasing the fuel yield and settled. After rough filtering out through a drum filter, the developed filter cake is transferred to a pellet press through a screw tunnel by conveying screw. In the pellet press, besides the pellets, pressed-out liquid additionally arises, which virtually contains all of the components of the previous steps. It is collected and periodically again pumped back into the reactor together with new or previously recovered vegetable oil, respectively, for complete utilization.

The pellets are transferred into a furnace or steam generator, optimized for this mode of energy carrier, respectively, in which the organic components are then combusted to $CO_2$ and water. Due to the high energy content of the vegetable oil, therein, correspondingly high energy amounts can be released. The generated water steam is advantageously utilized as a heating medium—for example for preheating the vegetable oil—potential excesses can be converted into electricity. Additionally, energy from the oxidation of iron hydroxides to hematite contained in the red mud is released. The remaining ash which is neutral or can be adjusted to a slightly basic pH value is subsequently deposited or can be used as a filler, building material, soil improver or mineral fertilizer after reduction and separation of the iron mineral.

The invention claimed is:

1. Method for transesterification of at least one component including at least one ester group with at least one component including at least one hydroxyl group,
   comprising;
   red mud, produced by a process consisting of the Bayer process used for aluminum production, to the method as a reaction-promoting component.

2. Method according to claim 1,
   characterized by the following steps:
   a) mixing the component including at least one ester group, the component including at least one hydroxyl group, and the red mud;
   b) heating and/or mixing the generated mixture for the duration of a predetermined time interval; and
   c) separating at least one first liquid phase from at least one second phase, wherein the liquid phase includes at least one carboxylic acid alkyl ester and the second phase includes at least dealkalized red mud.

3. Method according to claim 1,
   characterized in that
   the component including at least one ester group comprises a vegetable oil.

4. Method according to claim 1,
characterized in that
the component including at least one hydroxyl group comprises at least one compound of the group of the $C_1$ to $C_4$ monoalcohols.

5. Method according to claim 1,
characterized in that
at least one component is dissolved in a solvent and/or functions itself as a solvent.

6. Method according to claim 2,
characterized in that
in step a), first the component including at least one hydroxyl group is mixed with the red mud and subsequently an admixture of the component including at least one ester group is effected.

7. Method according to claim 2,
characterized in that
a temperature of at least one of the components is adjusted to a predetermined temperature value before admixture thereof.

8. Method according to claim 2,
characterized in that
the mixture is heated to about 60° C. in step b) for the duration of a time interval of about 60 minutes and/or at least partially mixed.

9. Method according to claim 2,
characterized in that
after step a), a fourth component is collected, which includes at least one component gaseous at room temperature and normal pressure.

10. Method according to claim 2,
characterized in that
the method includes an additional step d) after step b), which includes the collective separation of at least one fifth and one sixth component from the mixture, wherein the fifth component includes at least one compound of the group of the $C_1$ to $C_4$ monoalcohols and the sixth component includes at least water.

11. Method according to claim 10,
characterized in that
step d) includes at least one variation of temperature and/or pressure conditions.

12. Method according to claim 11,
characterized in that
the variation of the temperature conditions includes regulation of the temperature value to about 98° C.

13. Method according to claim 11,
characterized in that
the variation of the temperature conditions includes regulation of the temperature value to about 80° C., and the variation of the pressure conditions includes regulation of the pressure value to a value greatly decreased with respect to normal pressure, preferably below 250 hPa.

14. Method according to claim 10,
characterized in that
the method includes an additional step e) after step d), in which the fifth and sixth components collectively separated in step d) are separated.

15. Method according to claim 14,
characterized in that
step e) includes at least one process for separating homogeneous mixtures, especially an extractive distillation process.

16. Method according to claim 15,
characterized in that
the process for separating homogeneous mixtures includes an entrainer.

17. Method according to claim 2,
characterized in that
step c) includes at least one distillation and/or filtering and/or sedimentation and/or decantation process.

18. Method according to claim 17,
characterized in that
at least one sedimentation process includes separation of red mud sediments.

19. Method according to claim 18,
characterized in that
at least one filtering process includes a filtering step by means of red mud sediments.

20. Method according to claim 17,
characterized in that
at least one filtering process includes a filtering step by means of a vacuum filter.

21. Method according to claim 20,
characterized in that
the vacuum filter is formed in multiple stages.

22. Method according to claim 19,
characterized in that
at least a part of a filter cake produced by the filtering step is thermally utilized by combustion.

23. Method according to claim 22,
characterized in that
plastic and/or wood and/or biological waste is admixed with the filter cake before thermal utilization.

24. Method according to claim 22,
characterized in that
thermal energy arising in thermal utilization is supplied to at least one of the method steps a) to c) and/or optionally d) and/or e).

25. Method according to claim 2,
characterized in that
an additional step f) after step c) includes separation of at least one component including at least glycerin.

26. Method according to claim 25,
characterized in that
after step f), in a further step g), the at least one component including at least glycerin is separated into at least two degrees of quality.

27. Method according to claim 2,
characterized in that
after step c), in a further step h), at least one salt of at least one carboxylic acid containing sodium ions is separated from at least one separated phase.

28. The method according to claim 27, wherein the at least one salt of at least one carboxylic acid (soap) containing sodium ions, separated in step h), can be used as a plant treating agent.

29. The method according to claim 28, wherein the at least one salt of at least one carboxylic acid containing sodium ions is diluted with at least one solvent.

30. The method according to claim 27, wherein the at least one salt of at least one carboxylic acid containing sodium ions separated in step h) can be used as a detergent, especially in cleaning and/or washing agents.

31. The method according to claim 2, wherein the dealkalized red mud separated in step c) can be used as an iron-contributing component of an iron fertilizer.

32. The method according to claim 31, wherein the iron fertilizer includes at least limestone.

33. The method according to claim 3, wherein the vegetable oil is rape oil and/or palm oil and/or soya oil.

34. The method according to claim 16, wherein the entrainer is glycerin and/or paraffin oil and/or ethane diol.

35. The method according to claim 29, wherein the solvent is water.

* * * * *